(12) United States Patent
Tong

(10) Patent No.: US 10,792,685 B2
(45) Date of Patent: Oct. 6, 2020

(54) LIQUID SUPPLY FOR AN ELECTRONIC SMOKING DEVICE

(71) Applicant: FONTEM HOLDINGS 1 B.V., Amsterdam (NL)

(72) Inventor: Xinliang Tong, Beijing (CN)

(73) Assignee: FONTEM HOLDINGS 1 B.V., Amsterdam (NL)

( * ) Notice: Subject to any disclaimer, the term of this patent is extended or adjusted under 35 U.S.C. 154(b) by 48 days.

(21) Appl. No.: 15/766,775

(22) PCT Filed: Oct. 8, 2015

(86) PCT No.: PCT/CN2015/091485
§ 371 (c)(1),
(2) Date: Apr. 6, 2018

(87) PCT Pub. No.: WO2017/059571
PCT Pub. Date: Apr. 13, 2017

(65) Prior Publication Data
US 2018/0297047 A1    Oct. 18, 2018

(51) Int. Cl.
*A24F 40/10*     (2020.01)
*B05B 11/00*     (2006.01)
(Continued)

(52) U.S. Cl.
CPC ............ *B05B 11/007* (2013.01); *A24F 40/10* (2020.01); *A24F 47/00* (2013.01); *A24F 47/008* (2013.01);
(Continued)

(58) Field of Classification Search
CPC .. A24F 47/00–008; A24F 40/00; A24F 40/10; A61M 15/06
See application file for complete search history.

(56) References Cited

U.S. PATENT DOCUMENTS 5,423,793 A   6/1995   Isono et al.
5,877,390 A   3/1999   Kuriyama et al.
(Continued)

FOREIGN PATENT DOCUMENTS

CN   2076137 U      5/1991
CN   101818823 A    9/2010
(Continued)

OTHER PUBLICATIONS

International Search Report and Written Opinion for International Patent Application No. PCT/CN2015/091485, filed Oct. 8, 2015 for Fontem Holdings 2 B.V. et al, dated Mar. 25, 2016. 12 pages.
(Continued)

*Primary Examiner* — Michael H. Wilson
*Assistant Examiner* — Yana B Krinker
(74) *Attorney, Agent, or Firm* — Perkins Coie LLP; Kenneth H. Ohriner

(57) ABSTRACT

A liquid supply for an electronic smoking device has a liquid reservoir (110) within a housing (100) for holding a liquid. A buffering channel (120) within or on the housing (100) connects into the liquid reservoir (110) via a port (130). A sealing member (140) is fitted within the buffering channel (120) and provides a movable or slidable seal in the buffering channel (120). Upon expansion of a gas within the liquid reservoir (110) and/or a gaseous component within the liquid, the sealing member (140) moves within the buffering channel (120) to increase the effective volume of the liquid reservoir (110) and compensate for the change in pressure. Over-pressure and under-pressure conditions in the liquid reservoir are reduced or avoided.

20 Claims, 6 Drawing Sheets

(51) Int. Cl.
*A24F 47/00* (2020.01)
*A61M 15/06* (2006.01)
*A61M 11/04* (2006.01)

(52) U.S. Cl.
CPC ......... *A61M 15/06* (2013.01); *B05B 11/0054* (2013.01); *A61M 11/042* (2014.02); *A61M 2205/3375* (2013.01); *A61M 2205/8206* (2013.01)

(56) References Cited

U.S. PATENT DOCUMENTS

| | | | |
|---|---|---|---|
| 6,003,737 A | 12/1999 | Mascitelli | |
| 6,164,501 A | 12/2000 | Stradella | |
| 8,689,805 B2 | 4/2014 | Hon | |
| 8,910,641 B2 * | 12/2014 | Hon | H02J 7/0045 131/273 |
| 9,038,642 B2 | 5/2015 | Liu | |
| 9,420,829 B2 | 8/2016 | Thorens et al. | |
| 10,004,870 B2 | 6/2018 | Yamada et al. | |
| 10,143,234 B2 | 12/2018 | Hon | |
| 2010/0307518 A1 | 12/2010 | Wang | |
| 2011/0036363 A1 | 2/2011 | Urtsev et al. | |
| 2011/0094523 A1 | 4/2011 | Thorens et al. | |
| 2013/0161351 A1 | 6/2013 | Eini et al. | |
| 2013/0228191 A1 | 9/2013 | Newton et al. | |
| 2014/0076310 A1 | 3/2014 | Newton | |
| 2014/0109921 A1 | 4/2014 | Chen et al. | |
| 2014/0144429 A1 * | 5/2014 | Wensley | A61M 15/06 128/200.14 |
| 2014/0190496 A1 | 7/2014 | Wensley et al. | |
| 2014/0196728 A1 | 7/2014 | Lisan et al. | |
| 2015/0027470 A1 | 1/2015 | Kane et al. | |
| 2015/0173417 A1 * | 6/2015 | Gennrich | A24D 1/042 131/329 |
| 2015/0272216 A1 | 10/2015 | Dai et al. | |
| 2016/0255876 A1 | 9/2016 | Rostami | |
| 2018/0080559 A1 | 3/2018 | Li et al. | |
| 2018/0297047 A1 | 10/2018 | Tong | |
| 2019/0117921 A1 | 4/2019 | Bender et al. | |

FOREIGN PATENT DOCUMENTS

| | | | |
|---|---|---|---|
| CN | 102655773 A | 9/2012 | |
| CN | 202525085 U | 11/2012 | |
| CN | 103083752 A | 5/2013 | |
| CN | 202949973 U | 5/2013 | |
| CN | 103180053 A | 6/2013 | |
| CN | 203152481 U | 8/2013 | |
| CN | 103732280 A | 4/2014 | |
| CN | 203737489 U | 7/2014 | |
| CN | 103960781 A | 8/2014 | |
| CN | 203927998 U | 11/2014 | |
| CN | 104223369 A | 12/2014 | |
| CN | 204048047 U | 12/2014 | |
| CN | 104305529 A | 1/2015 | |
| CN | 104394721 A | 3/2015 | |
| CN | 104432542 A | 3/2015 | |
| CN | 104544570 A | 4/2015 | |
| CN | 204426694 U | 7/2015 | |
| CN | 104839892 A | 8/2015 | |
| CN | 204560966 U | 8/2015 | |
| CN | 102387719 B | 3/2016 | |
| EP | 2614731 A1 | 7/2013 | |
| EP | 2719416 A1 | 4/2014 | |
| GB | 2524295 A | 9/2015 | |
| WO | WO-2017028295 A1 * | 2/2017 | ........... A24F 47/008 |

OTHER PUBLICATIONS

European Patent Office extended European Search Report for European Application No. 15905669.6; dated Dec. 3, 2019; 9 pages.

* cited by examiner

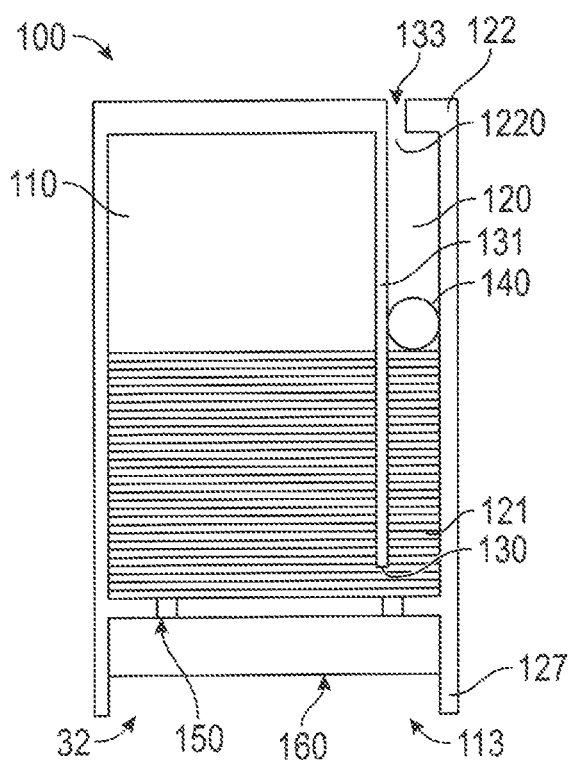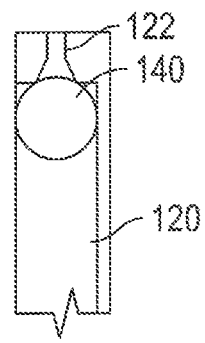
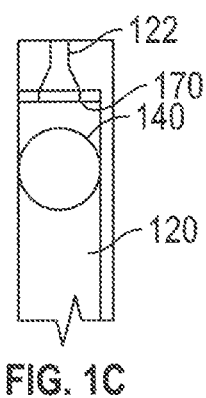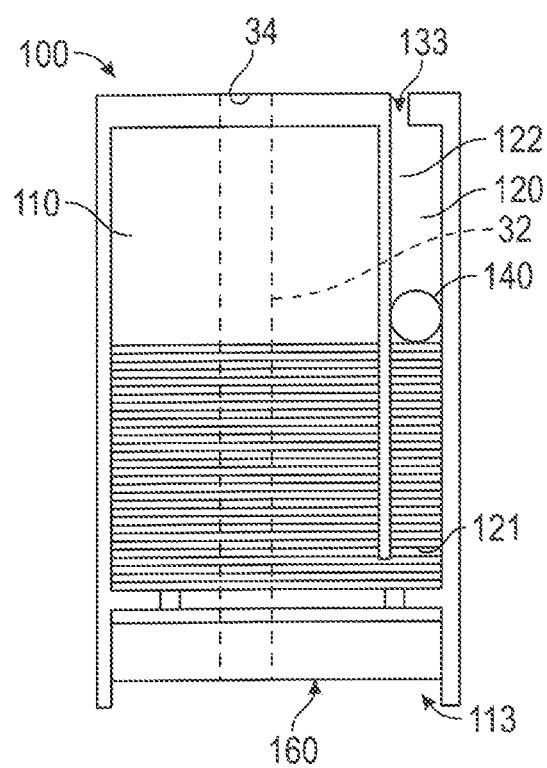

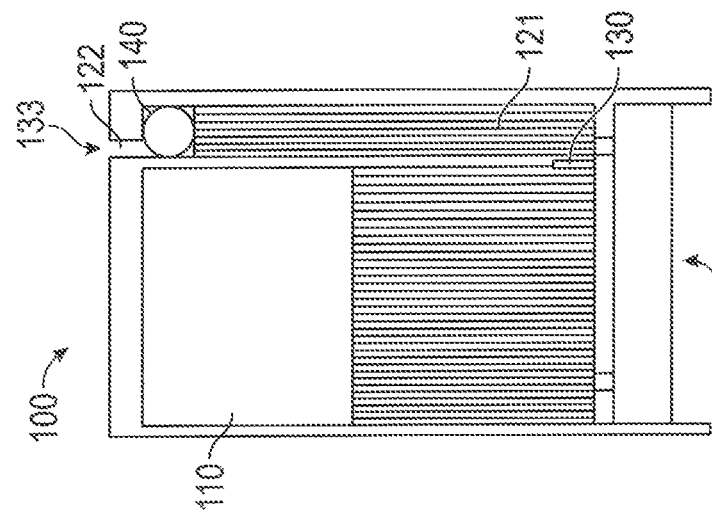
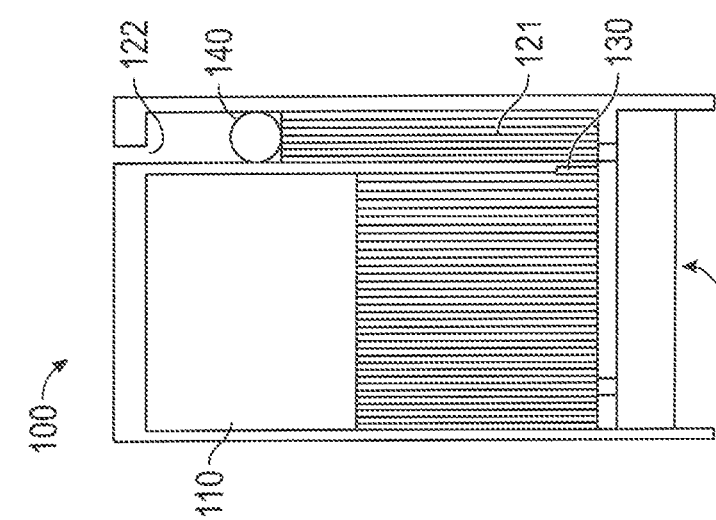
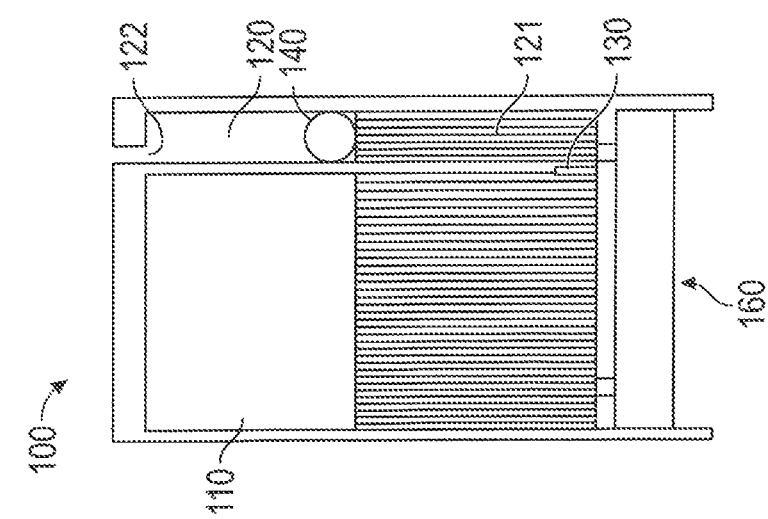

LIQUID SUPPLY FOR AN ELECTRONIC SMOKING DEVICE

TECHNICAL FIELD

The field of the invention is liquid supplies for electronic smoking devices, including electronic cigarettes.

BACKGROUND

Some liquid supplies for electronic smoking devices use a rigid housing having a liquid outlet port and an air inlet. Air flows into the housing via the air inlet as liquid flows out of the housing to a vaporizer which vaporizes the liquid. As a result, the pressure in the housing generally remains equal to ambient pressure. However, the air flowing into the housing may mix with the liquid in the housing. In this case an increase in ambient temperature can cause an over-pressure condition in the housing. Under certain conditions, the over-pressure condition in the housing may cause liquid to leak out of the housing. Correspondingly, an under-pressure condition in the housing may interfere with liquid flow out of the housing.

BRIEF DESCRIPTION OF THE DRAWINGS

FIG. 1A is a schematic illustration of a liquid supply having a straight buffering channel.

FIG. 1B is a schematic illustration of a sealing member coupled to a tapering vent opening.

FIG. 1C is a schematic illustration of a sealing member coupled to a tapering vent opening having a flexible layer.

FIG. 2 is a schematic illustration of a liquid supply having a central aerosol passage;

FIGS. 5A to 5C show the liquid supply of FIGS. 1A to 4C in a balanced condition, a moderate over-pressure condition, and an extreme over-pressure condition.

DETAILED DESCRIPTION

A liquid supply for an electronic smoking device includes a housing that encloses a space or reservoir for holding liquid, and a buffering portion or channel. Liquid and/or gas can flow between the reservoir and the buffering channel via a port connecting them. A sealing member is movable within the buffering channel while also sealing against the buffering channel. If pressure in the housing rises with rising temperature, the sealing member moves in a first direction which increases the effective combined volume of the reservoir and the buffering channel in the buffering channel. This movement reduces pressure in the reservoir, compensating for the pressure increase resulting from a temperature increase. When ambient temperature drops, the sealing member moves in a second direction which decreases the effective combined volume of the reservoir and the buffering channel. Pressure within the reservoir is consequently better maintained in balance with ambient air pressure. The buffering channel may be a straight, spiral or toroidal buffering channel or groove. The sealing member may be provided as a ball, a cylinder, or a section of lithium based grease. The sealing member may also be pre-tensioned by an elastic element.

Figure 8:
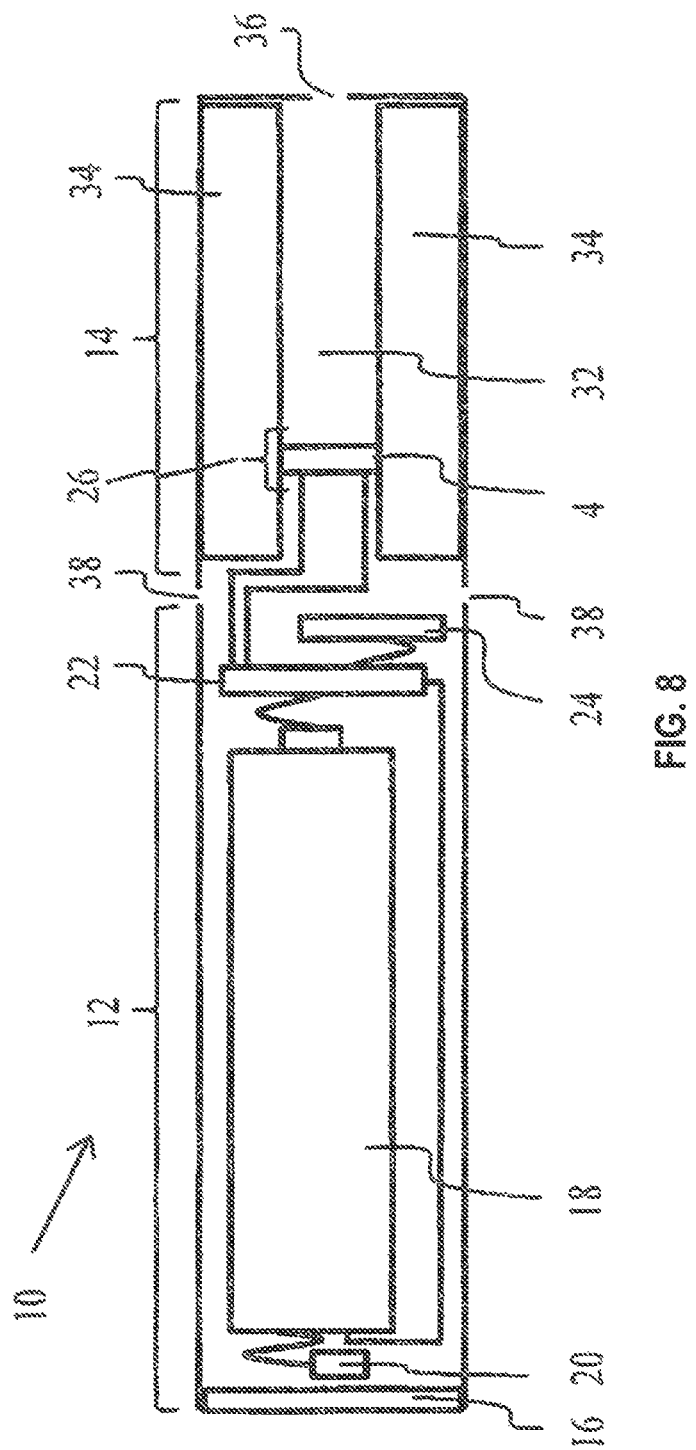
FIG. 8 is a schematic illustration of a central aerosol channel electronic smoking device.

Referring initially to FIG. 8, an electronic cigarette 10 typically has a housing comprising a cylindrical hollow tube having an end cap 16. The cylindrical hollow tube may be single piece or a multiple piece tube. In FIG. 8, the cylindrical hollow tube is shown as a two piece structure having a battery section or assembly 12 and an vaporizer/liquid supply section or assembly 14. Together the battery section 12 and the vaporizer/liquid supply section 14 form a cylindrical tube which is approximately the same size and shape as a conventional cigarette, typically about 100 mm with a 7.5 mm diameter, although lengths may range from 70 to 150 or 180 mm, and diameters from 5 to 20 mm.

The battery section 12 and vaporizer/liquid supply section 14 are typically made of steel or hardwearing plastic and act together with the end caps to provide a housing to contain the components of the e-cigarette 10. The battery section 12 and a vaporizer/liquid supply section 14 may be configured to fit together by a friction push fit, a snap fit, or a bayonet attachment, magnetic fit, or screw threads. The end cap 16 is provided at the front end of the main body 12. The end cap 16 may be made from translucent plastic or other translucent material to allow an LED 20 positioned near the end cap to emit light through the end cap. The end cap can be made of metal or other materials that do not allow light to pass.

An air outlet may be provided in the end cap, at the edge of the outlet next to the cylindrical hollow tube, anywhere along the length of the cylindrical hollow tube, or at the connection of the battery section 12 and the vaporizer/liquid supply section 14. FIG. 8 shows a pair of air outlets 38 provided at the intersection between the battery section 12 and the vaporizer/liquid supply section 14.

A battery 18, a light emitting diode (LED) 20, control electronics 22 and optionally an airflow sensor 24 are provided within the battery section 12. The battery 18 is electrically connected to the control electronics 22, which is electrically connected to the LED 20 and the airflow sensor 24. In this example the LED 20 is at the front end of the main body 12, adjacent to the end cap 16 and the control electronics 22 and airflow sensor 24 are provided in the central cavity at the other end of the battery 18 adjacent the vaporizer/liquid supply section 14.

The airflow sensor 24 acts as a puff detector and detects a user puffing or sucking on the vaporizer/liquid supply section 14 of the e-cigarette 10. The airflow sensor 24 can be any suitable sensor for detecting changes in airflow or air pressure such a microphone switch including a deformable membrane which moves in response to variations in air pressure. Alternatively the sensor may be a Hall element or an electro-mechanical sensor. The control electronics 22 are also connected to a vaporizer 26. In the example shown, the vaporizer 26 includes a heating coil 28 which is wrapped around a wick 30 extending across a central passage 32 of the vaporizer/liquid supply section 14.

The coil 28 may be positioned anywhere in the vaporizer and may be transverse or parallel to the liquid supply. The wick 30 and heating coil 28 do not completely block the central passage 32. Rather an air gap is provided on either side of the heating coil 28 enabling air to flow past the heating coil 28 and the wick 30. The vaporizer may alternatively use other forms of heating elements, such as ceramic heaters, or fiber or mesh material heaters. Nonresistance heating elements such as sonic, piezo and jet spray may also be used in the vaporizer in place of the heating coil.

The central passage 32 is surrounded by a cylindrical liquid supply 34 with the ends of the wick 30 abutting or extending into the liquid supply 34. The wick 30 may be a porous material such as a bundle of fiberglass fibers, with liquid in the liquid supply 34 drawn by capillary action from the ends of the wick 30 towards the central portion of the wick 30 encircled by the heating coil 28.

The liquid supply 34 may alternatively include wadding soaked in liquid which encircles the central passage 32 with the ends of the wick 30 abutting the wadding. In other embodiments the liquid supply 34 may comprise a toroidal cavity arranged to be filled with liquid and with the ends of the wick 30 extending into the toroidal cavity. Any of the liquid supplies of FIGS. 1-7 may be used in the e-cigarette 10 as an alternative to the liquid supply 34.

An air inhalation port 36 is provided at the back end of the vaporizer/liquid supply section 14 remote from the end cap 16. The inhalation port 36 may be formed from the cylindrical hollow tube vaporizer/liquid supply section 14 or may be formed in an end cap.

In use, a user sucks on the e-cigarette 10. This causes air to be drawn into the e-cigarette 10 via one or more air outlets, such as air outlets 38 and to be drawn through the central passage 32 towards the air inhalation port 36. The resulting change in air pressure or flow rate is detected by the airflow sensor 24 which generates an electrical signal that is passed to the control electronics 22. In response to the signal, the control electronics 22 activates the heating coil 28 which causes liquid present in the wick 30 to be vaporized creating an aerosol (which may comprise gaseous and liquid components) within the central passage 32. As the user continues to suck on the e-cigarette 10, this aerosol is drawn through the central passage 32 and inhaled by the user. At the same time the control electronics 22 also activates the LED 20 causing the LED 20 to light up which is visible via the translucent end cap 16 simulating the appearance of a glowing ember at the end of a conventional cigarette. As liquid present in the wick 30 is converted into an aerosol more liquid is drawn into the wick 30 from the liquid supply 34 by capillary action and thus is available to be converted into an aerosol through subsequent activation of the heating coil 28.

Some e-cigarettes are intended to be disposable and the electric power in the battery 18 is intended to be sufficient to vaporize the liquid contained within the liquid supply 34 after which the e-cigarette 10 is thrown away. In other embodiments the battery 18 is rechargeable and the liquid supply is refillable. In the cases where the liquid supply 34 is a toroidal cavity, this may be achieved by refilling the liquid supply via a refill port. In other embodiments the vaporizer/liquid supply section 14 of the e-cigarette 10 is detachable from the battery section 12 and a new vaporizer/liquid supply section 14 can be fitted with a new liquid supply 34 thereby replenishing the supply of liquid. In some cases, replacing the liquid supply 34 may involve replacement of the heating coil 28 and the wick 30 along with the replacement of the liquid supply 34.

The replacement liquid supply 34 may be in the form of a cartridge having a central passage 32 through which a user inhales aerosol. In other embodiments, aerosol may flow around the exterior of the cartridge to an air inhalation port 36.

Of course, in addition to the above description of the structure and function of a typical e-cigarette 10, variations also exist. For example, the LED 20 may be omitted. The airflow sensor 24 may be placed adjacent the end cap 16 rather than in the middle of the e-cigarette. The airflow sensor 24 may be replaced with a switch which enables a user to activate the e-cigarette manually rather than in response to the detection of a change in air flow or air pressure.

Different types of vaporizers may be used. Thus for example, the vaporizer may have a heating coil in a cavity in the interior of a porous body soaked in liquid. In this design aerosol is generated by evaporating the liquid within the porous body either by activation of the coil heating the porous body or alternatively by the heated air passing over or through the porous body. Alternatively the vaporizer may use a piezoelectric vaporizer to create an aerosol either in combination or in the absence of a heater.

FIG. 1A shows a liquid supply having a straight buffering channel 120. The liquid supply 32 in this example includes a tubular housing 100, a liquid reservoir 110 formed by a first portion of the housing 100, a straight buffering channel 120 formed by a second portion of the housing 100 and a sealing member 140 fitted within the buffering channel 120. The buffering channel 120 is arranged alongside of the liquid reservoir 110. The buffering channel 120 includes a first end 121 which connects into the liquid reservoir 110 via a port or opening 130 in the wall 131 separating the liquid reservoir from the buffering channel 120. The port 130 may alternatively be located at an intermediate position above the first end 121. A vent opening 133 at the second end 122 of the buffering channel 120 connects to the ambient environment, directly or through an opening in the housing of the electronic smoking device 10.

The tubular housing 100 includes an outlet port 150 for delivering liquid to the vaporizer. As shown in FIG. 1A, the sealing member 140 may be in the shape of a ball which moves within the buffering channel 120 while also sealing against the sidewalls of the buffering channel, to compensate for pressure changes in the reservoir. In this case the ball diameter is nominally larger than the diameter of the buffering channel, to provide a seal which prevents liquid from escaping past the ball. In some embodiments the ball may allow gas or air to move through or alongside of the ball, while preventing similar movement of liquid. FIGS. 1-7 show the reservoir in a vertical and upright position, so that the entire space in the buffering channel 120 below the sealing member or ball is filled with liquid. With the reservoir on its side, for example as installed in an electronic cigarette, the buffering channel 120 may be entirely filled with air or gas. In either case however, the liquid supply operates in the same way.

The inner surface of the vent opening 133 can be tapered to engage the ball shaped sealing member as shown in FIG. 1B. FIG. 1C shows a flexible layer 170 attached to the inner side of the vent opening 133 which slightly deforms upon contact with the sealing member 140 and restores it original shape when the sealing member leaves the flexible layer. The flexible layer 170 may be gas permeable, but not liquid permeable, to allow gas or air to move into and out of the space in the buffering channel between the vent opening 133 and the sealing member. Liquid stored within the liquid reservoir 110 is delivered to the vaporizer through an outlet port 150. The outlet port 150 can be provided with a toroid opening. In the example shown in FIG. 1A, the wall 127 of the tubular housing 100 forms a recess 113 adapted to fit in a liquid conducting component 160, for example a liquid conducting pad.

The electronic smoking device 10 may have an aerosol channel 32 provided either through the longitudinal axial of the tubular housing 100 or arranged along the perimeter of the tubular housing 100 to conduct the aerosol from the vaporizer 26 through the liquid supply to the inhalation port 36 or the mouth piece. In FIGS. 2 and 3, a straight aerosol channel 32 extends through the tubular housing. In FIGS. 4A and 4C, a spiral aerosol channel 33 extends around the perimeter of the tubular housing.

In FIG. 5A, liquid in the liquid reservoir 110 and the buffering channel 120 are maintained at the same level when the liquid reservoir is maintained at a predetermined pressure. With an increase in ambient temperature and an expansion of the gas in the liquid reservoir, the liquid within the buffer channel 120 rises along with the sealing member 140, as shown in FIG. 5B. The volume of the buffer channel can be configured to accommodate, for example 1%~5% of the total volume of the liquid reservoir. FIG. 5C shows an extreme situation where the liquid level in the buffering channel rises to the highest level and the sealing member 140 is pushed against and seals off the vent opening 133 of the second end of the buffering channel 120. When ambient temperature drops, the liquid level in the buffering channel drops until the pressure restores to the original predetermined pressure. The sealing member may slide along the walls of the buffering channel, to accommodate pressure changes, while also preventing liquid from leaking past the sealing member and out of the vent opening 133.

Figure 3A:
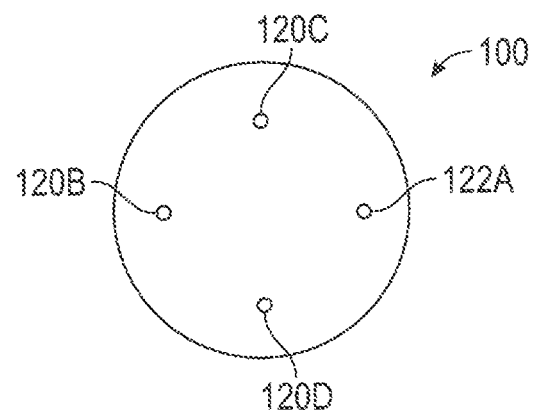
FIG. 3A is a top schematic illustration of a liquid supply having four buffering channels.
Figure 3B:
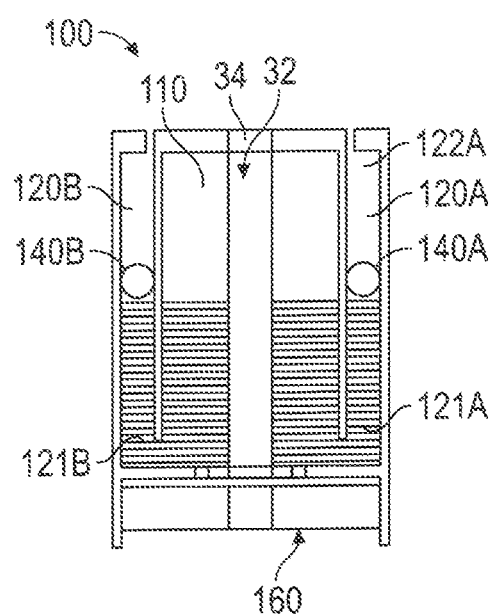
FIG. 3B is a sectional schematic illustration of a liquid supply having four buffering channels.
Figure 4A:
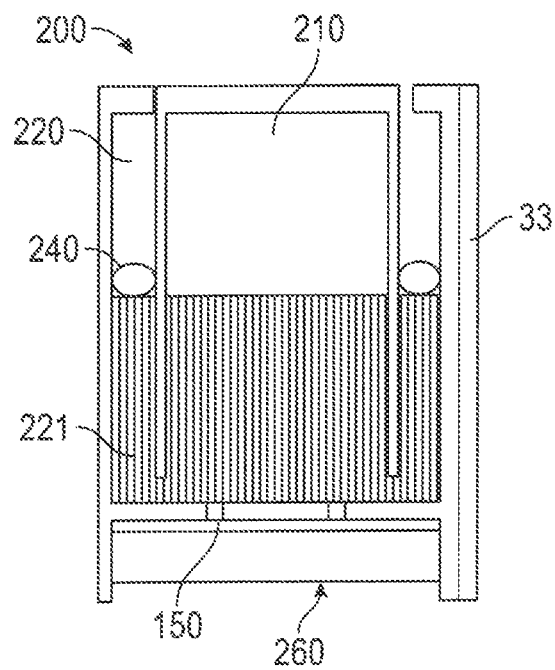
FIG. 4A is a sectional schematic illustration of a liquid supply having a toroidal buffering groove and an aerosol channel arranged on the perimeter of a tubular housing.
Figure 4B:
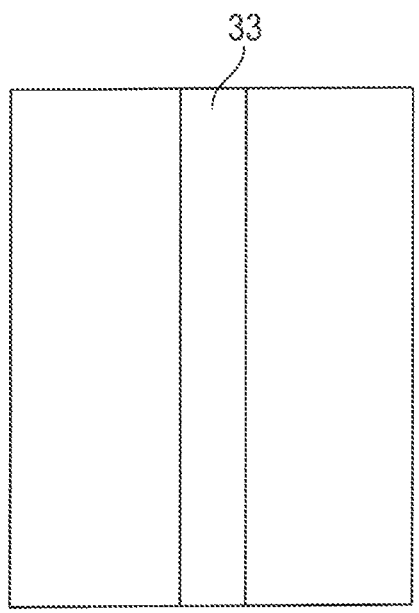
FIGS. 4B and 4C are schematic illustrations a liquid supply having a straight aerosol channel arranged on the perimeter of the housing and a spiral aerosol channel arranged on the perimeter of the housing.
Figure 4C:
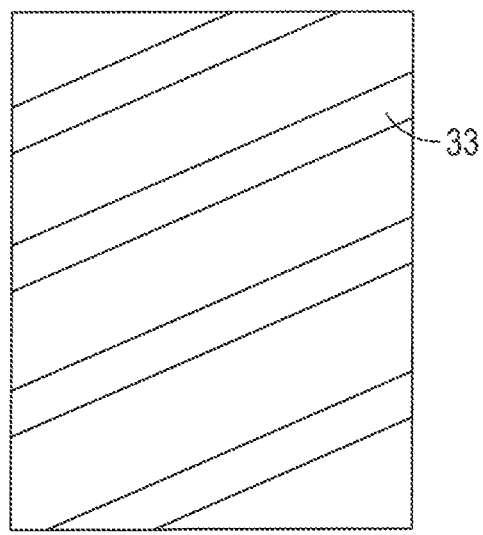

In a further embodiment shown in FIGS. 3A and 3B, four buffering channels 120A-120D are provided and spaced evenly around the liquid reservoir 110. Other buffering channel arrangements, such as two, three, five or six buffering channels spaced evenly or unevenly are also possible variations. The cross section shape of the buffering channel 120 may be round, oval, triangle, square, rectangle or polygonal. Crescent and other specialty shapes may optionally be used as may be convenient to fit within the vaporizing device 10. The liquid reservoir may be provided in any shape or configuration as may be useful in an electronic cigarette or vaporizing device. Typically a cylindrical or toroidal shape is used.

Figure 3C:
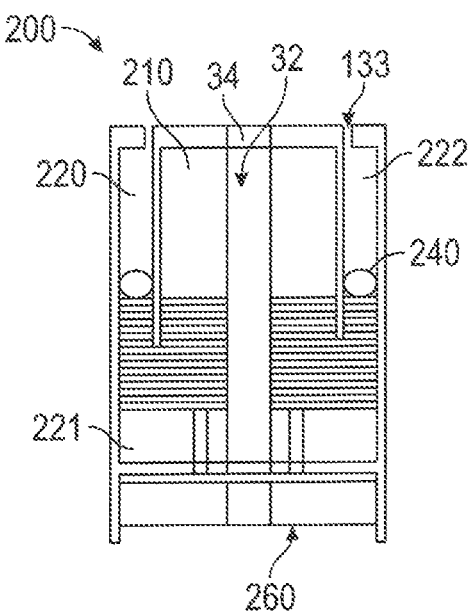
FIG. 3C is a sectional schematic illustration of a liquid supply having a toroidal buffering groove.

FIGS. 3C and 4A show a liquid supply having a toroidal buffering groove. Similar to the embodiments described above, the liquid supply has a tubular housing 200 that forms a liquid reservoir 210 and a toroidal buffering groove 220 around the liquid reservoir 210. The liquid reservoir supplies liquid to an vaporizer though an outlet port 250 and optionally a liquid guiding component. A toroidal sealing member is fitted within the toroidal groove. The toroidal buffering groove 220 has a first end that connects into the liquid reservoir 210 through at least one opening, and a second end having at least one annular slot or several orifices that connect the buffering groove directly to the atmosphere or through the housing of the device 10.

Figure 6:
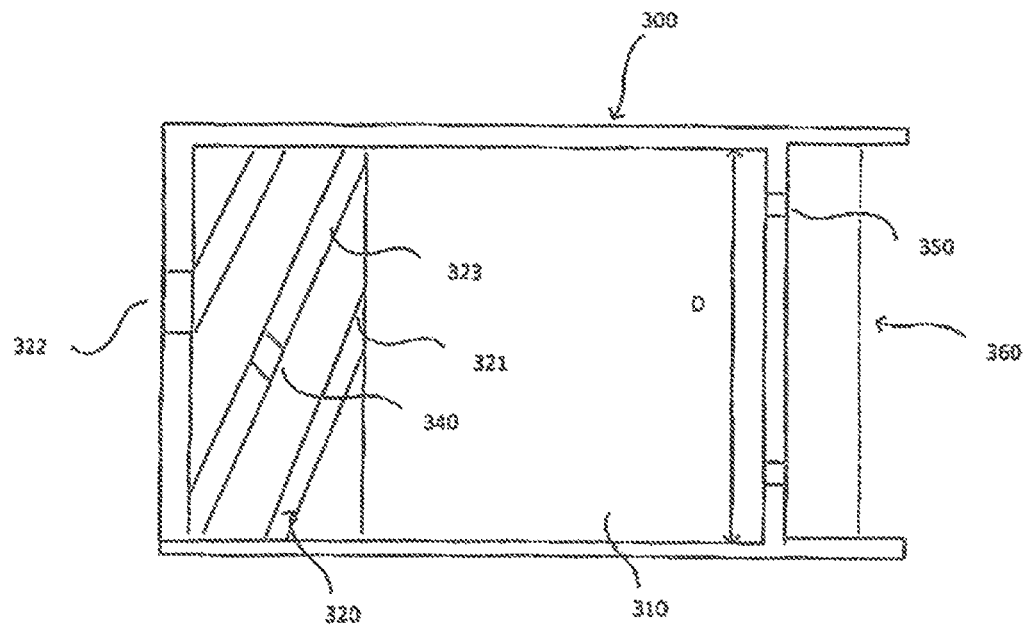
FIG. 6 is a schematic illustration of a liquid supply having a spiral buffering channel.

FIG. 6 shows a liquid supply 34 having a spiral buffering channel 321. In this embodiment, the liquid supply 34 has a tubular housing 300 forming a liquid reservoir 310 next to an outlet port 350, and a spiral buffering channel distal to the outlet port. The spiral buffering channel has a first end 321 that connects into the liquid reservoir 310, a second end 322 that connects directly with the atmosphere or through the housing of the device 10. A spiral path 323 extends between the first end 321 and the second end 322. The spiral path 323 occupies the entire radial dimension D of the liquid reservoir 310. In this embodiment, the second end 322 of the spiral buffering channel generally extends along the longitudinal axial of the tubular body. The spiral buffering channel 320 allows for a horizontal arrangement of the liquid supply so that the longitudinal axis of the liquid supply is parallel to the longitudinal axis of the device 10.

Figure 7:
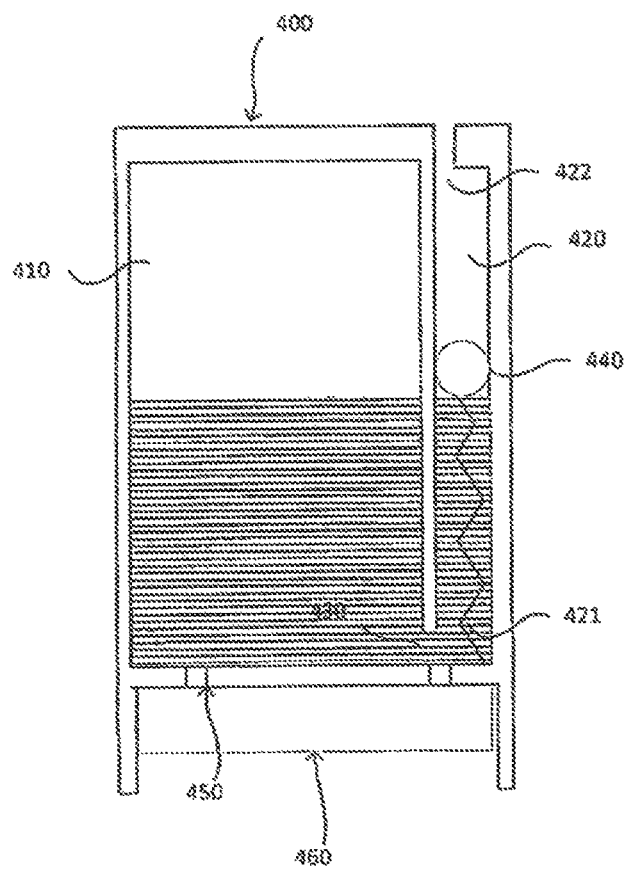
FIG. 7 is a schematic illustration of a liquid supply having a pre-tensioned buffering component.

FIG. 7 is a schematic illustration of a liquid supply similar to those described above and further including a spring loaded sealing member. In FIG. 7, a liquid supply includes a tubular housing 400 forming a liquid reservoir 410 and a buffering channel 420 that connects into the liquid reservoir via an opening 430. A sealing member 440 is fitted within the buffering channel 420. One side of the sealing member 440 is connected to the bottom of the tubular housing via an elastic element 421 and is pre-tensioned by the elastic element, such as a spring. The spring causes the sealing member to resist movement caused by changes in pressure in the reservoir. In this case, the pressure in the reservoir may be limited to a selected range above and/or below ambient pressure, depending on the spring constant of the spring selected.

The spring-loaded sealing member 440 may also be used in sealing members for the multiple buffering channel arrangement as shown in FIGS. 3A and 3B and the toroidal sealing member arrangement as shown in FIG. 3C.

The sealing member 140, 240, 340 and 440 can be formed from rigid material such as plastic, metal, or from flexible material such as rubber, latex, silicon, and synthetic rubber, or the sealing member can have a rigid material core and a coating of flexible material. The sealing member can also be gel-form substance such as lithium based grease. The material that forms the tubular housing can be transparent or opaque. The relative positions of the elements shown, such as the liquid outlet 150, the liquid conducting element 160, and others, are examples only and may be changed depending design parameters.

Thus, various embodiments have been shown and described. Various modifications and substitutions may be made without deviating from the spirit and scope of the invention. Accordingly, the invention should not be limited, except by the appended claims and their equivalents.

I claim:

1. An electronic smoking device, comprising,
a housing having an inlet and an outlet;
a liquid supply, a vaporizer, and control electronics electrically connected with the vaporizer;
wherein the liquid supply comprises:
a liquid reservoir to hold liquid, the liquid reservoir having outlet port for delivering liquid to the vaporizer;
a buffering channel connecting into the liquid reservoir via a buffering channel opening a port;
a vent opening at a first end of the buffering channel; and
a sealing member within the buffering channel between the buffering channel opening and the vent opening, with the sealing member forming a seal within the buffering channel and with the sealing member movable within the buffering channel to compensate for pressure changes in the liquid reservoir.

2. The electronic smoking device of claim 1 further comprising a wall separating the liquid reservoir from the buffering channel, and the buffering channel opening extending through in the wall to allow liquid to move between liquid reservoir and the buffering channel.

3. The electronic smoking device of claim 1 with the buffering channel comprising at least one spiral channel.

4. The electronic smoking device of claim 1 further comprising a flexible material covering the vent opening.

5. The electronic smoking device of claim 1 with the vent opening having a contoured inner surface and with the sealing member having a complimentary inner surface.

6. The electronic smoking device of claim 1 with the liquid supply comprising a cartridge attachable to the housing or insertable into the housing.

7. The electronic smoking device of claim 1 with the volume of the buffering channel equal to 1% to 5% of the volume of the liquid reservoir.

8. The electronic smoking device of claim 1 wherein the sealing member is gas permeable but not liquid permeable.

9. The electronic smoking device of claim 1 wherein the vent is at a first end of the buffering channel and the buffering channel opening is at a second end of the buffering channel.

10. An electronic smoking device, comprising,
a vaporizer; and
a liquid supply including:
a liquid reservoir having an outlet port for delivering liquid to the vaporizer;
a buffering channel connecting into the liquid reservoir via a buffering channel opening;
a vent opening at a first end of the buffering channel, the buffering channel opening at a second end of the buffering channel; and
a sealing member movable within the buffering channel between the buffering channel opening and the vent opening.

11. The electronic smoking device of claim 10 further comprising a wall separating the liquid reservoir from the buffering channel, and the buffering channel opening through in the wall to allow liquid to move between liquid reservoir and the buffering channel.

12. The electronic smoking device of claim 10 with the buffering channel comprising at least one spiral channel.

13. The electronic smoking device of claim 12 with the at least one spiral channel around an outside surface of the liquid reservoir.

14. The electronic smoking device of claim 10 with the vaporizer and the control electronics in a housing, and the liquid supply comprising a cartridge attachable to the housing or insertable into the housing, and the cartridge having a vapor outlet.

15. The electronic smoking device of claim 10 with the buffering channel having a volume equal to 1% to 5% of the volume of the liquid reservoir.

16. The electronic smoking device of claim 10 wherein the sealing member is gas permeable but not liquid permeable.

17. The electronic smoking device of claim 10 further comprising a spring engaging the sealing member.

18. The electronic smoking device of claim 10 with the sealing member comprising a section of grease.

19. An electronic smoking device, comprising,
a housing having an inlet and an outlet;
a liquid supply, and a vaporizer;
wherein the liquid supply comprises:
a liquid reservoir to hold liquid;
a buffering channel connecting into the liquid reservoir via a buffering channel opening, the buffering channel comprising at least one spiral channel around an outside surface of the liquid reservoir;
a vent opening at a first end of the buffering channel; and
a sealing member within the buffering channel between the buffering channel opening and the vent opening, with the sealing member forming a seal within the buffering channel and with the sealing member movable within the buffering channel to compensate for pressure changes in the liquid reservoir.

20. The electronic smoking device of claim 19 further including control electronics electrically connected with the vaporizer.

\* \* \* \* \*

UNITED STATES PATENT AND TRADEMARK OFFICE
CERTIFICATE OF CORRECTION

PATENT NO. : 10,792,685 B2
APPLICATION NO. : 15/766775
DATED : October 6, 2020
INVENTOR(S) : Xinliang Tong Page 1 of 1

It is certified that error appears in the above-identified patent and that said Letters Patent is hereby corrected as shown below:

In the Specification

In Column 4, Line 25, delete "32".

In the Claims

In Column 6, Line 55, in Claim 1, delete "a port".

In Column 6, Line 66, in Claim 2, delete "in".

In Column 7, Line 36, in Claim 11, delete "in".

Signed and Sealed this
Twenty-sixth Day of January, 2021

Drew Hirshfeld
*Performing the Functions and Duties of the*
*Under Secretary of Commerce for Intellectual Property and*
*Director of the United States Patent and Trademark Office*